DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED JULY 6, 1976

948 O.G. 7

T948,011

DETERMINATION OF AMINE OR AMIDE NITROGEN CONTENT IN VEGETABLE OIL

James C. Kuck, New Orleans, La., assignor to the United States of America as represented by the Secretary of Agriculture

Filed Jun. 9, 1975, Ser. No. 585,214
Int. Cl. C11b *3/04;* G01n *33/26*
U.S. Cl. 23—230 R
No Drawings. 7 Pages of Specification

Minute amounts of nitrogen in amines or amides in vegetable oils are determined. A sample of vegetable oil is weighed into an extraction flask and hydrochloric acid and ethanol are added. After refluxing for about 12 hours, aqueous hydrochloric acid is added and the mixture is refluxed for about 6 more hours. The contents of the flask are then transferred to a separatory funnel and allowed to stand until separation is attained. The bottom layer containing the ethanol and aqueous hydrochloric acid is then collected and the oil layer returned for further extraction and refluxing by the same method. This procedure is repeated twice and each time the bottom layer is collected. The collected bottom layer material is then digested by the Kjeldahl method, titrated with .1N sodium hydroxide, and the percent nitrogen extracted is calculated. The method is useful in detecting and measuring traces of toxic substance is vegetable oils.